United States Patent
Williams et al.

(10) Patent No.: US 7,281,413 B2
(45) Date of Patent: Oct. 16, 2007

(54) ACOUSTIC METHOD FOR DETERMINING THE VISCOSITY AND/OR SURFACE TENSION OF A LIQUID

(75) Inventors: Roger O. Williams, Paradise Valley, AZ (US); James Chiao, Saratoga, CA (US); Humphrey W. Chow, Cupertino, CA (US); Michael J. Forbush, Hollister, CA (US); Andrew M. Rose, Mountain View, CA (US)

(73) Assignee: EDC Biosystems, Inc., Milpitas, CA (US)

( * ) Notice: Subject to any disclaimer, the term of this patent is extended or adjusted under 35 U.S.C. 154(b) by 136 days.

(21) Appl. No.: 11/088,436

(22) Filed: Mar. 24, 2005

(65) Prior Publication Data
US 2005/0193805 A1   Sep. 8, 2005

Related U.S. Application Data

(63) Continuation-in-part of application No. 10/290,626, filed on Nov. 7, 2002, now Pat. No. 6,925,856.

(51) Int. Cl.
*G01N 11/00* (2006.01)

(52) U.S. Cl. .............. 73/54.01; 73/53.01; 73/49.2

(58) Field of Classification Search ........... 73/64.48, 73/51.41, 64.53, 579, 597, 599, 602, 618, 73/620, 624, 629, 54.01, 49.2, 53.01
See application file for complete search history.

(56) References Cited

U.S. PATENT DOCUMENTS

| 4,391,129 | A | * | 7/1983 | Trinh et al. | 73/64.48 |
| 4,512,183 | A | * | 4/1985 | Alexander | 73/64.48 |
| 5,303,030 | A | * | 4/1994 | Abraham et al. | 356/482 |
| 6,563,588 | B2 | * | 5/2003 | Behroozi | 356/477 |
| 6,596,239 | B2 | | 7/2003 | Williams et al. | |

FOREIGN PATENT DOCUMENTS

WO    WO/0136959    * 5/2001

OTHER PUBLICATIONS

U.S. Appl. No. 10/290,626, filed Nov. 7, 2002, Williams et al.

(Continued)

*Primary Examiner*—Hezron Williams
*Assistant Examiner*—Rodney Frank
(74) *Attorney, Agent, or Firm*—Donald J. Pagel

(57) ABSTRACT

The present invention comprises a noncontact method for measuring viscosity and/or surface tension information of a liquid in a liquid containment structure. The steps of the method include exciting a surface of the liquid with an excitation burst of acoustic energy that causes the surface to oscillate; generating a positional data set comprised of a plurality of positional measurements related to the detected position of the surface at a plurality of times after the surface is excited; generating a frequency domain data set from the positional data set, the amplitude spectrum of the frequency domain data set comprising information about the oscillation frequency of at least one vibrational mode of the of the surface as it oscillates; and processing the frequency domain data set and/or the positional data set to yield information about the surface tension and/or viscosity of the liquid. A Fast Fourier Transform technique may be used in generating the frequency domain data set.

21 Claims, 10 Drawing Sheets

OTHER PUBLICATIONS

Vibrational Modes of a Circular Membrane—(DRUMS!), http://kettering.edu/~drussell/Demos/MembraneCircle/Circle, pp. 1-3, printed from web site Feb. 4, 2005.

MATLAB Signal Processing Toolbox, The Math Works, Inc., pp. 6-115 thru 6-118, 6-166 (Dec. 1996).

* cited by examiner

ACOUSTIC METHOD FOR DETERMINING THE VISCOSITY AND/OR SURFACE TENSION OF A LIQUID

This application is a continuation-in-part of application Ser. No. 10/290,626, filed Nov. 7, 2002, now U.S. Pat. No. 6,925,856.

FIELD OF THE INVENTION

The present invention relates to a method for measuring viscosity and/or surface tension information of a liquid without contacting the liquid. In particular, the present invention relates to measuring viscosity and/or surface tension information of the liquid using acoustic energy.

BACKGROUND

Many methods for the precision transfer and handling of fluids are known and used in a variety of commercial and industrial applications. The presently burgeoning industries of the biotechnology and biopharmaceuticals are particularly relevant examples of industries requiring ultra-pure fluid handling and transfer techniques.

Various current fluid transfer methods require contacting the fluid with a transfer device, e.g., a pipette, a pin, or the like. Such contact methods dramatically increase the likelihood of contamination. Many biotechnology procedures, e.g., polymerase chain reaction (PCR), have a sensitivity that results in essentially a zero tolerance for contamination. Thus, noncontact methods for fluid transfer are desirable.

An exemplary non contact method for ejecting liquid droplets to a target location is described in U.S. Pat. No. 6,596,239, issued Jul. 22, 2003 and entitled "Acoustically Mediated Fluid Transfer Methods And Uses Thereof." This fine acoustic liquid ejection technique, however, may be improved by compensating for liquids having varying surface tension and viscosity values. It has been observed that such an acoustic liquid ejector can be limited or adversely affected by varying viscosity and surface tension values of the sample liquid to be transferred. Indeed, volume and trajectory of droplet ejection depend upon the acoustic stimuli as well as the viscosity and surface tension of the liquid to be transferred. If the viscosity and surface tension are unknown, then the volume and trajectory of the transferred fluid may vary in an unknown manner. However, with knowledge of the viscosity and surface tension properties of each sample liquid, the acoustic stimuli used to transfer small amounts of fluid may be adjusted accordingly, improving the accuracy and precision of the transfer of that fluid. Thus, it would be advantageous to determine the viscosity and surface tension properties of each fluid prior to ejection. It is also desirable to determine this product in a manner that is easily automated.

Examples of conventional methods for measuring the viscosity of a fluid include capillary tube and rotary viscometers. These techniques require direct contact with the liquid to be measured which may introduce contamination when making multiple measurements.

Examples of conventional methods for measuring surface tension include: sessile drop, pendant drop, maximum bubble pressure, capillary height, the Du Noüy ring, and the Wilhelmy plate methods. All of these techniques have the disadvantage of requiring contact with the fluid or removal of a sample of the fluid.

Examples of noncontact methods of measuring surface tension of sea water are described in Can Cinbis, "Noncontact Techniques for Measuring Surface Tension of Fluids," Doctoral Thesis, Stanford University, 1992. A first method involves measuring the water surface displacement caused by the radiation pressure associated with an acoustic pulse. The displacement is measured with a confocal optical microscope. The surface tension of the liquid is calculated from the measured values. The second method utilizes two ultrasonic transducers: the first transducer generates a wave and the second transducer measures the amplitude of the transient capillary wave a distance from the first transducer. The surface tension is calculated from the measured values. The technique, however, does not provide viscosity information.

None of the above described methods provide a noncontact method to measure viscosity and surface tension information as described herein.

SUMMARY OF THE INVENTION

The present invention comprises a noncontact method for measuring viscosity and/or surface tension information of a liquid in a liquid containment structure. The steps of the method include exciting a surface of the liquid contained in a container with an excitation burst of acoustic energy that causes the surface to oscillate; generating a positional data set comprised of a plurality of positional measurements related to the detected position of the surface at a plurality of times after the surface is excited; generating a frequency domain data set from the positional data set, the frequency domain data set comprising phase spectrum and amplitude spectrum data, with the amplitude spectrum comprising information for at least one vibrational mode of the of the surface as it oscillates; and processing the positional data set and/or the frequency domain data set to yield information about the surface tension and/or viscosity of the liquid.

The positional data set may be generated by reflecting short bursts of acoustic energy off the oscillating surface of the liquid and using the time of flight of the reflected waves as an indicator of the position of the surface. The frequency domain data set may be generated from the positional data set using a Fast Fourier Transform (FFT) technique. The frequency domain data set may be processed to yield a parameter such as the damped natural frequency of a vibrational mode which is then related to the surface tension of the liquid. The frequency domain data set may be further processed using an Inverse Fast Fourier Transform (IFFT) to yield a parameter such as the decay time constant, which is then related to the viscosity of the liquid. Under certain conditions, the positional data set may also be processed in the time domain to yield natural frequencies and decay time constants.

DETAILED DESCRIPTION OF THE INVENTION

The invention relates to methods of measuring viscosity and surface tension information of a liquid without contacting the liquid and in particular, to methods of measuring surface tension and viscosity information of the liquid using acoustic energy.

Figure 1A:
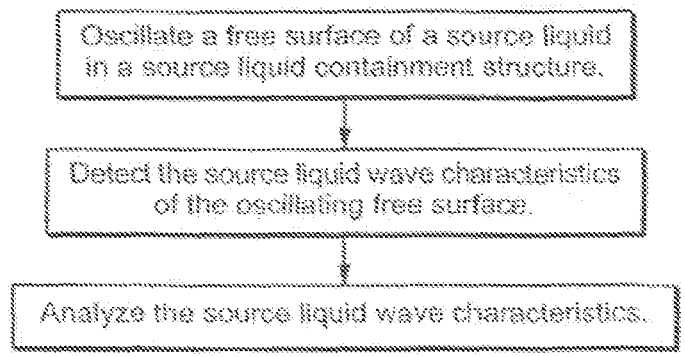
FIG. 1a is a block diagram illustrating the steps performed in one embodiment of the invention to measure viscosity and surface tension information of a sample liquid.
Figure 1B:
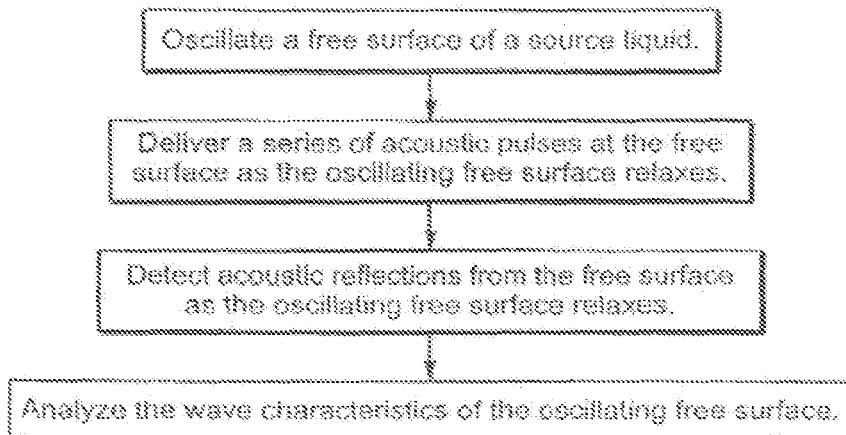
FIG. 1b is a block diagram illustrating the steps performed in another embodiment of the invention to measure viscosity and surface tension information of a sample liquid.

With reference to FIG. 1a, the method of the invention includes the following steps: (1) oscillate a free surface of a first or sample liquid, (2) detect the sample liquid wave characteristics of the oscillating free surface and (3) analyze the sample liquid wave characteristics. As indicated in FIG. 1b, one embodiment of the invention provides that the detecting step comprises delivering a series of acoustic pulses at the oscillating free surface as the oscillating free surface relaxes and detecting acoustic reflections from the oscillating free surface as it relaxes. Additionally, the step of analyzing the sample liquid wave characteristics may include comparing an attribute of the wave profile of the decaying oscillating free surface of the sample liquid with a candidate liquid attribute. The attribute may be, for example, a curve, and a curve fitting algorithm may be employed to match the measured sample liquid with a candidate liquid having known properties. Accordingly, the present invention provides a method for measuring viscosity and surface tension information without contacting the sample liquid.

Oscillating a Free Surface of a First Liquid

As indicated above, the first step of the method of the invention includes oscillating a free surface of a first or sample liquid whose viscosity and surface tension product is to be measured. Preferably, an acoustic energy wave is focused at or near the free surface of the sample liquid to urge the free surface upwards to form a temporary mound. The acoustic energy wave should be sufficient to urge or disturb the free surface upwards; but the acoustic energy wave should not exceed a threshold value which would cause liquid to be ejected. However, the threshold value can vary widely and depends on a number of other factors as discussed in U.S. Pat. No. 6,596,239.

Figure 2:
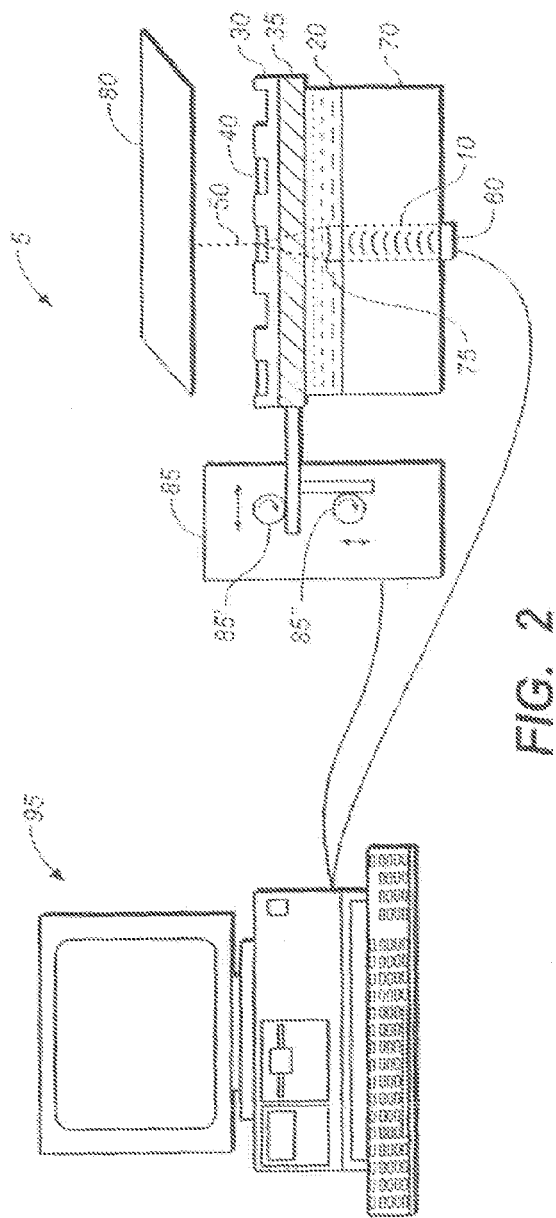
FIG. 2 is a schematic diagram illustrating a system for acoustically moving a portion of sample liquid in a sample liquid containment structure.
Figures 3A, 3B, 3C, 3D, 3E, 3F:
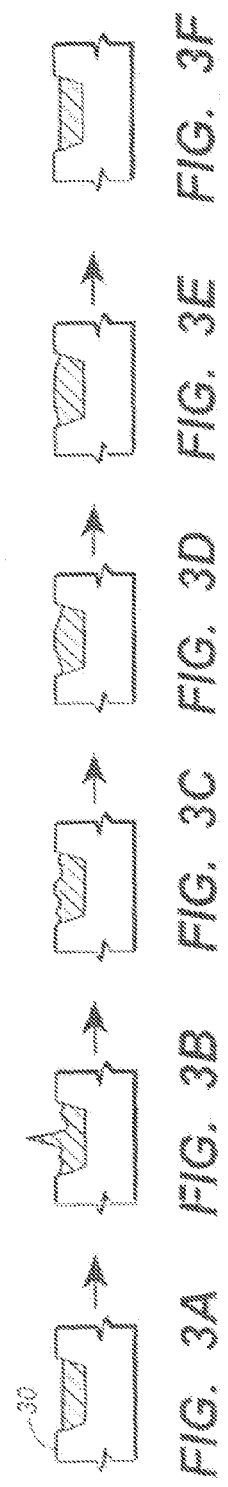
FIGS. 3a-3f illustrate an oscillating free surface of a sample liquid in a sample liquid containment structure relaxing over time.

An exemplary system 5 to perform the method of the invention is shown in FIG. 2. It includes at least one acoustic wave emitter 60 in electrical communication with a computer 95. During operation the acoustic liquid deposition emitter 60 generates an acoustic wave or beam 10 that can be propagated through an optional wave channel 70. The acoustic wave can be focused by lens 75 prior to propagating through coupling fluid 20 to optimize the energy of the acoustic wave or beam 10 upon the liquid/air interface (free surface) of source fluid 40. The acoustic wave 10 is propagated through a coupling medium 20 after which the wave is transmitted through source fluid containment structure 30 where the wave comes to focus at or near the surface of a pool of source fluid 40 thereby causing the liquid to urge upwards so as to form a mound.

The mound of liquid subsequently oscillates and relaxes until its oscillations can no longer be observed. FIGS. 3a-3f illustrate, in chronological order, oscillations of a free surface of liquid in a containment structure 30.

Examples of sample liquid containment structures include single and multi-well plates commonly used in molecular biology applications, capillaries (e.g., capillary arrays), and the like. However, other containers or structures may be used to hold a liquid to be ejected. Notably, the source fluid containment structure 30 is detachably affixed to a movable stage 35. The movable stage 35 is controlled by actuator mechanism 85 which contains a horizontal actuator 85' or a vertical actuator 85" or a combination of the two actuators to control the movement of the stage 35 in both the vertical and horizontal directions. The actuator 85 is typically in communication with computer 95 which controls the movement of the stage to select a source fluid 40 or to adjust focusing of the acoustic wave or beam 10 upon the source fluid 40. The computer may have implemented thereon various algorithms to adjust the focal length and energy of the acoustic wave emitter as well as control and manage the location of the acoustic wave emitter relative to a particular source fluid present in or on a source fluid containment structure. Accordingly, the system may be used to provide acoustic stimuli to cause the free surface to oscillate such that the surface tension and viscosity value may be determined. The system shown in FIG. 2 also may be used to cause a droplet 50 to be ejected from the liquid pool 40 towards a target substrate 80, as is described in U.S. Pat. No. 6,596,239.

In a preferred embodiment, a piezoelectric transducer is employed as an acoustic wave emitter. In one embodiment, a piezoelectric transducer comprises a flat thin piezoelectric element, which is constructed between a pair of thin film electrode plates. As is understood by those of skill in the art, when a high frequency and appropriate magnitude voltage is applied across the thin film electrode plates of a piezoelectric transducer, radio frequency energy will cause the piezoelectric element to be excited into a thickness mode oscillation. The resultant oscillation of the piezoelectric element generates a slightly diverging acoustic beam of acoustic waves. By directing the wave or beam onto an appropriate lens having a defined radius of curvature (e.g., a spherical lens, or the like), the acoustic beam can be brought to focus at a desired point. Acoustic energy is delivered for a short period of time to form the mound. A suitable short period of time is from 1 to 30 μs.

In one embodiment, a computer sends an analog voltage pulse to the piezoelectric transducer by an electrical wire. The voltage pulse can be controlled, for example, by a MD-E-201 Drive Electronics manufactured by Microdrop, GmbH, Muhlenweg 143, D-22844 Norderstedt, Germany. The electronics can control the magnitude and duration of the analog voltage pulses, and also the frequency at which the pulses are sent to the piezoelectric transducer. Each voltage pulse causes the generation of an acoustic wave from the piezoelectric transducer, which in turn is propagated through a coupling medium and into or through the source fluid thereby impinging on the surface of the source fluid. Such acoustic waves may be generated to urge the surface of the source fluid into an excited oscillating state.

The piezoelectric transducer may be in the form of a flat crystal disk, or other crystal designs, e.g., square, perforated disk, and the like. In a preferred embodiment, the piezoelectric transducer is a flat disk. Because many electronic circuits are designed for a 50 Ω(ohm) load, it is presently preferred to employ a 50 Ω transducer. While the materials for the piezoelectric element may vary greatly, a preferred material is a Navy Type I piezoelectric material disk element having a diameter D=0.039 inch or D=0.991 mm. Other shapes of piezoelectric crystals are also contemplated for use in the practice of the present invention.

Detecting of Oscillations in the Fluid Surface

Detection of the oscillating free surface of the source fluid is preferably performed using acoustic waves. For example, a series of acoustic pulses may be directed at the oscillating free surface as it relaxes. The pulses may be synchronously phased. The echoes or reflections of the pulses from the oscillating free surface are detected and recorded. In this manner, data is generated for each source or sample liquid.

Figure 4A:
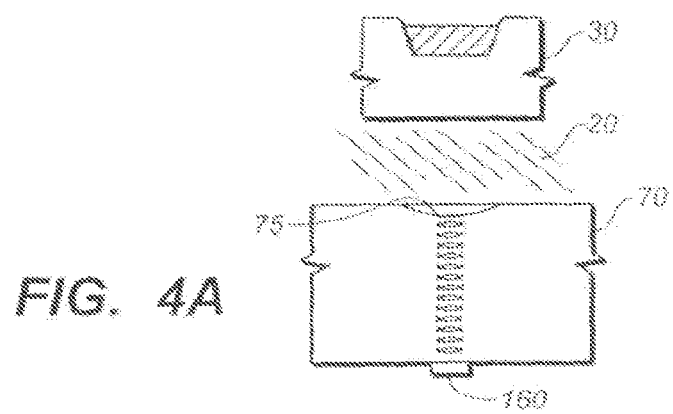
FIG. 4a is a schematic diagram illustrating an acoustic energy emitter having one piezoelectric element.

Various emitter configurations can be employed to carry out the detection step. An exemplary configuration is shown in FIG. 4a wherein a single transducer 160 is provided to emit and detect acoustic waves off the oscillating free surface. The emitter 160 may also be used for the oscillating step described above.

Figure 4B:
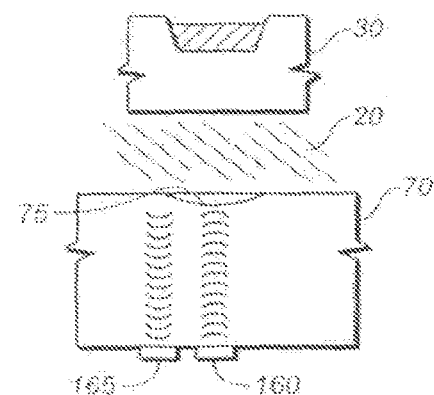
FIG. 4b is a schematic diagram illustrating an acoustic energy apparatus having two piezoelectric elements.
Figure 4C:
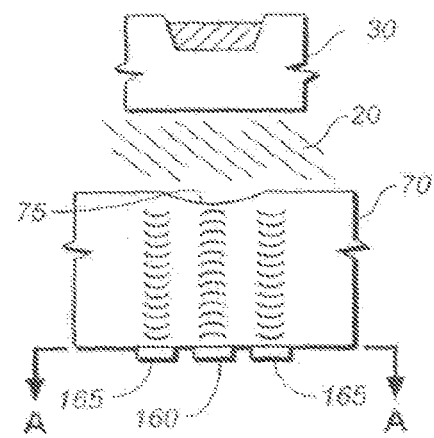
FIG. 4c is a schematic diagram illustrating an acoustic wave emitter having a central piezoelectric element and a second piezoelectric element circumferentially surrounding the first element.
Figure 4D:
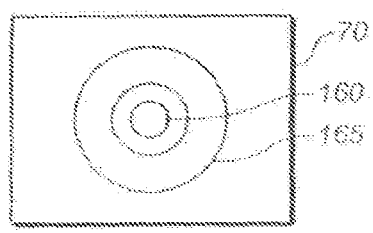
FIG. 4d is a bottom view of the apparatus illustrated in FIG. 4c taken along A-A.

FIG. 4b illustrates another embodiment having a secondary piezoelectric transducer 165. The secondary piezoelectric transducer 165 can be employed to detect the oscillations of the free surface of the fluid. The secondary piezoelectric transducer may be adjacent to a primary transducer 160 or it may be toroidal-shaped as shown in FIGS. 4c and 4d. Thus, a wide range of transducer configurations may be employed to direct and detect acoustic energy from the free surface. Additionally, at least one of the transducers may be used to deliver energy sufficient to eject a droplet of sample liquid.

Detection may also be performed by optically observing the oscillating free surface of the sample liquid. Optical detectors contemplated for use with the present invention include but are not limited to a camera, a photoelectric cell, and the like. For example, a laser or other light source can be directed at the surface of a source pool, and the scattering of the laser or other light caused by the oscillating free surface can be detected by one or more photoelectric cells coupled to a computer. Other optical detection methods known to those of skill in the art or developed in the future may be employed in order to detect the oscillating surface of the sample liquid.

Analyzing the Sample Liquid Wave Characteristics

Figure 5A:
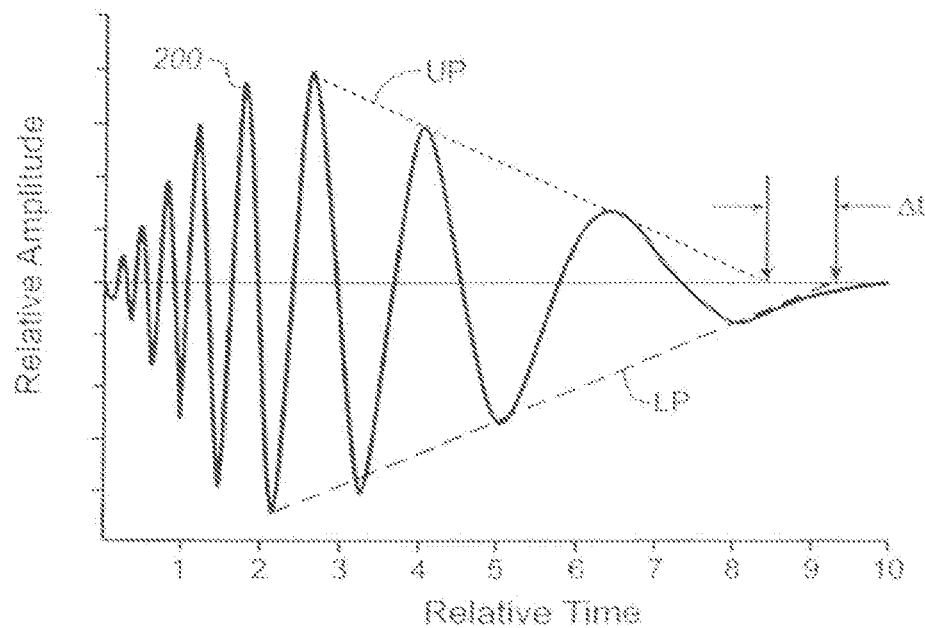
FIGS. 5a-5c are graphs showing echo data of an oscillating free surface of a liquid as the oscillating free surface relaxes.
Figure 5B:
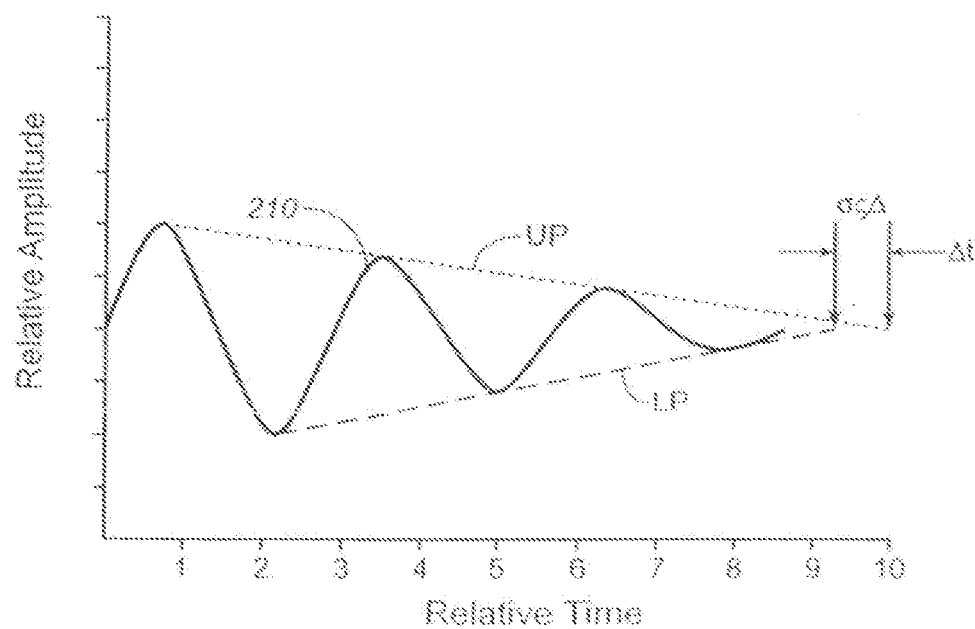
Figure 5C:
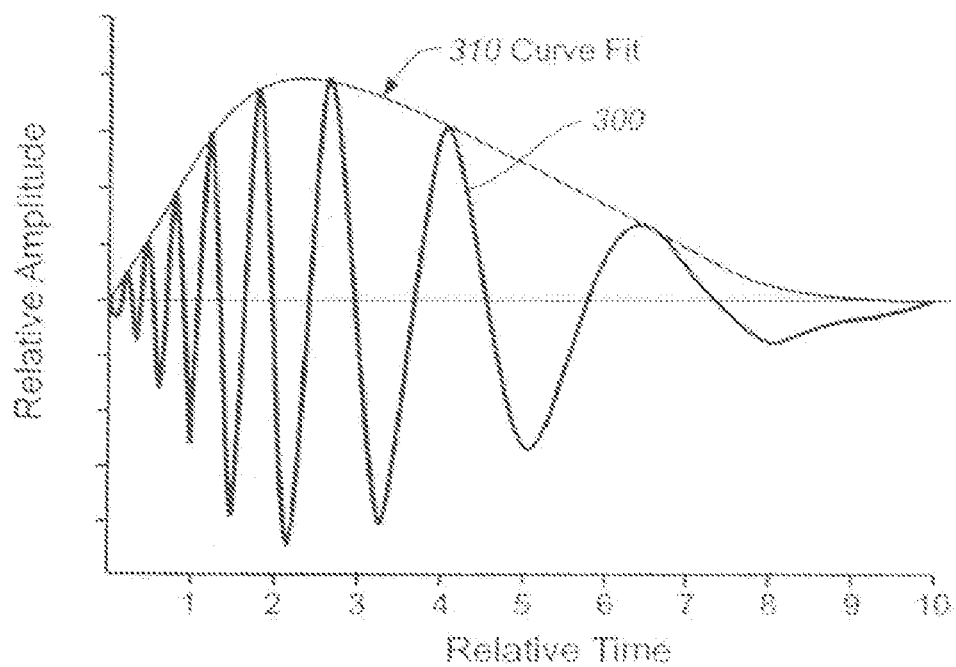

Once the wave characteristics of the oscillating free surface of the liquid have been detected or recorded, analysis of the echo data can begin. Examples of echo data for an oscillating free surface as it relaxes are shown in FIGS. 5a-5c.

The echo data or profiles may be analyzed or characterized in various ways. In one embodiment, an attribute (e.g., "Δt") may be defined and used to characterize the echo profile. The Δt shown in FIGS. 5a-5b is the distance along the horizontal axis where the upper peak maxim value (UP) and the lower peak maxim value (LP) intersect the horizontal axis. Δt corresponds to the viscosity-surface tension product of a liquid and varies with liquids having different viscosity and surface tensions.

After obtaining Δt for a sample liquid having an unknown viscosity and surface tension, the sample liquid's viscosity-surface tension information may be identified by comparing its Δt with candidate values contained in a library or database. The candidate values have known properties including, for example, wave dampening rates for a given acoustic stimuli, viscosity and surface tension information, density information, droplet ejection in response to certain acoustic stimuli, and other properties which may be useful in acoustic droplet ejection. Thus, by analyzing the sample liquid in accordance with the foregoing, various information about the sample liquid is obtained including its viscosity and surface tension information.

Curve fitting is another suitable technique to select or identify a candidate liquid. FIG. 5c shows the echo data 300 having a curve fit 310. Curve fit 310 may be estimated as a polynomial and matched with a candidate having a similar polynomial. The matching algorithms that can be used for this purpose range from simple least squares approach (linear regression) to a neural network-based approach as well as other curve fitting techniques. Such methods are discussed in various text books including Chapter 14 of "Mathematical Statistics and Data Analysis" by John Rice, Duxbury Press and Chapter 4 of "Neural Networks for Pattern Recognition" by Christopher Bishop, Oxford University Press. Accordingly, a sample liquid can be analyzed using the above described technique to obtain its viscosity and surface tension information without contacting the liquid.

Notwithstanding the above, there may be situations when data from a sample does not correlate with any candidate. In this situation, where known data fitting techniques do not provide a solution, the properties of two candidates having faster and slower dampening profiles (or attributes) may be averaged to predict or estimate the viscosity/surface tension product for the sample liquid. In another variation, the system may simply default to a predetermined viscosity surface tension product when the library does not provide an appropriate candidate. Still other data fitting and matching techniques may be utilized as is known to those skilled in the art.

The measuring technique provided by the present invention has various useful applications. An exemplary application of the present invention is to optimize droplet ejection based on measuring the product of the viscosity and surface tension of the liquid to be ejected. An acoustic ejector (e.g., the acoustic ejector 5 of FIG. 2) may be optimized by determining an optimal amount of energy (an acoustic stimulus) to be applied to eject a droplet of liquid. Various parameters have been observed to affect droplet ejection including viscosity and surface tension information. It follows that by measuring the viscosity and surface tension information (e.g., the product) of the sample liquid prior to ejection, the acoustic stimuli can be adjusted to compensate for liquids having various surface tensions and viscosity which would otherwise decrease the accuracy of the droplet ejection.

The viscosity and surface tension information, for example, can be supplied to the computer 95 and statistically compared with measured data to best estimate what energy should be applied to achieve a desired droplet. Suitable algorithms include maximum likelihood algorithms. Such algorithms determine the power which will most likely provide a desired droplet feature based on past data. Examples of droplet features or characteristics include size, mass, angle of ejection, spray threshold, etc.

Suitable algorithms for determining optimal values are known and can be found in various known texts. It is also to be understood that other information may used to determine an optimal power. Indeed, user input, density, liquid level, and other parameters may be input into an algorithm to determine the optimal power output. Furthermore, as each droplet is ejected, a database is updated with new information. The information is fed back to the computer to provide a better setting for subsequent droplet ejection.

Figure 1C:
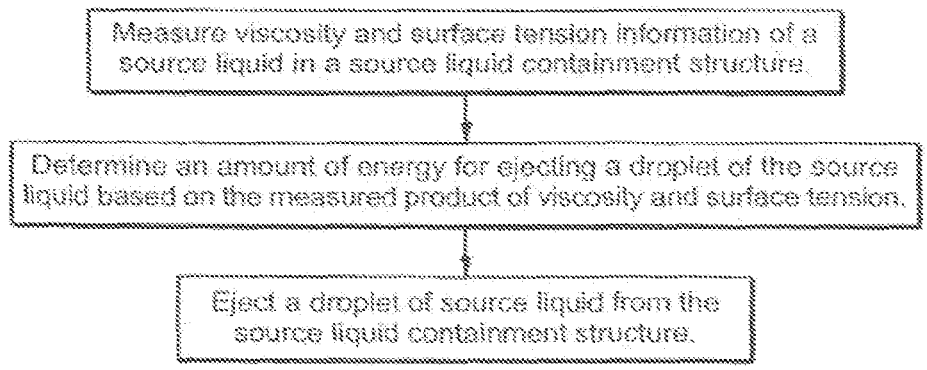
FIG. 1c is a block diagram illustrating the steps performed in a variation of the invention to acoustically eject a droplet of sample liquid based on measuring viscosity and surface tension information of the sample liquid.

The steps of an acoustic ejector that utilize the viscosity and surface tension information of the present invention are shown in FIG. 1*c*. First, the viscosity and surface tension product are measured. Next, an optimized acoustic stimulus is determined based on the viscosity and surface tension information. The optimized acoustic stimulus is determined by comparing the measured product with past measured values of actual droplets ejected. A feedback algorithm is preferably employed to continuously optimize droplet ejection as more information is obtained.

Examples of liquids to be ejected include water, mixtures, solutions, solder, photoresists, biological compounds and other substances which can be ejected or deposited onto a target substrate. Preferably, the acoustic ejector is used to eject liquids useful in biological or chemical applications.

Stimulus-Response Method for Determining Surface Tension and/or Viscosity

The method described with respect to FIGS. 1*a* and 1*b* can be modified to yield surface tension and/or viscosity information more directly. In this embodiment, the position of a surface of a sample liquid is tracked as the surface oscillates. The positional data is then processed to yield the surface tension and/or viscosity information.

Figure 6:
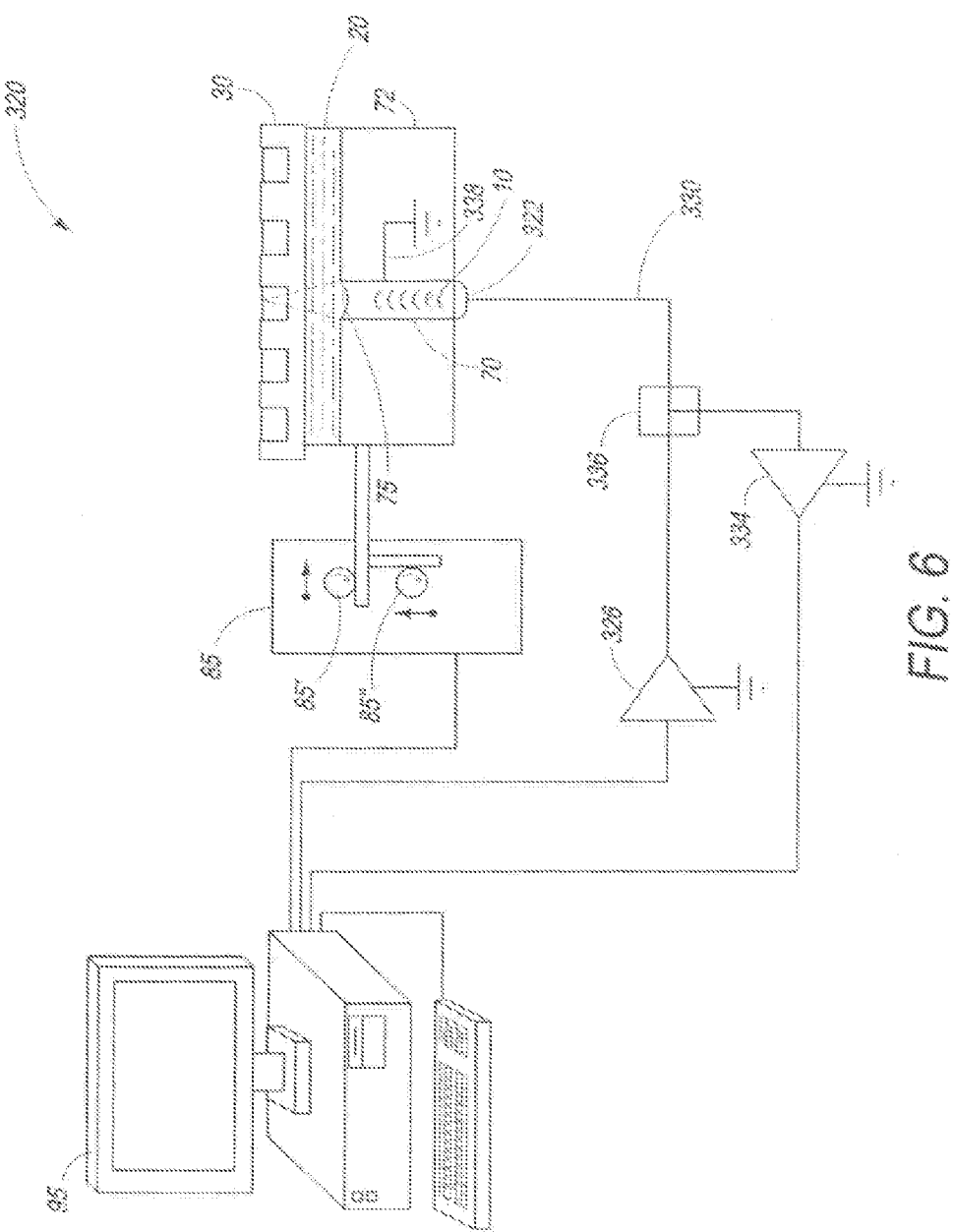
FIG. 6 is a schematic diagram illustrating a system for acoustically measuring the position of the surface of a sample liquid while it oscillates.

FIG. 6 illustrates a system 320 for collecting the positional data. The system 320 is only a slight modification of the system 5 illustrated in FIG. 2. Therefore, elements in FIG. 6 that are identical to elements described previously with respect to FIG. 2 are labeled with the same numerals that were used previously in FIG. 2.

In FIG. 6, the acoustic deposition emitter 60 shown in FIG. 2 has been renamed an acoustic transducer 322 to emphasize its role as both a detector of acoustic energy signals as well as a generator of acoustic energy. The transducer 322 generates a wave of acoustic energy 10 in the same manner as was described previously for the emitter 60, but the transducer 322 also acts as detector of reflected acoustic signals by converting acoustic energy back into an electrical signal. The emitters 60 and 160 described previously with respect to FIGS. 2 and 4*a*, respectively, also performed a detection function.

In FIG. 6, the computer 95 controls the delivery of electrical signals to an amplifier 326 to activate the transducer 322. A transmission line 330, such as a coaxial cable, delivers pulses of alternating current generated by the amplifier 326 to the transducer 322. Since the transducer 322 is utilized for both generating and detecting acoustic waves, a receiver 334 is provided to receive electrical signals from the transducer 322. Because the receiver 334 is sensitive and cannot withstand the large output from the amplifier 326, a means for protecting the receiver 334 from the amplifier output signal is needed. Preferably, this protection is provided by a broadband RF directional coupler 336 positioned between the amplifier 326 and the receiver 334 to separate the amplifier output from the input to the receiver 334 at all times. Alternatively, many other circuit designs that provide such protection to the receiver 334 may be used. A ground lead 338 connected to the waveguide 70 grounds the transducer 322 and is part of the transmission line 330. In one embodiment, the amplifier 326 comprises a class A linear amplifier, and the receiver 334 comprises a digitizing signal capture device.

In the preferred embodiment, the transducer 322 comprises a piezoelectric crystal (e.g., 20 MHz crystal, cylindrical in shape with a 3 mm diameter active area) attached to the proximal end of the waveguide 70. The waveguide 70 is secured inside a movable support structure 72, and the movable support structure can be moved in the vertical and horizontal directions by the actuator mechanism 85. Preferably, the waveguide 70 comprises aluminum and is a solid cylinder in shape. One of ordinary skill in the art would appreciate that the waveguide may be comprised of other acoustic conductive materials, such as silicon, silicon nitride, silicon carbide, sapphire, fused quartz, certain glasses, or many other acoustically conductive materials. The distal end of the waveguide is configured with a concave surface which serves as the lens 75 for focusing the acoustic wave into a focused beam. Preferably, the lens 75 is adapted to focus the acoustic wave 10 at or near the surface of the sample liquid. In a representative embodiment, the surface of the sample liquid (e.g. surface 344 in FIG. 7) needs to be approximately 7.5 mm from the lens 75 for focus to be achieved. This distance is ensured by using the vertical actuator 85" to move the movable support structure 72 up or down until adequate focus is achieved.

Figure 8:
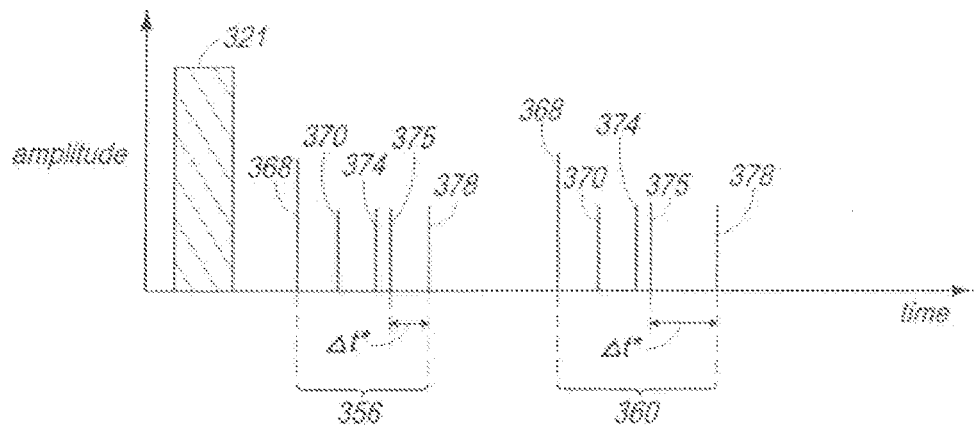
FIG. 8 is a schematic diagram illustrating the acoustic signals used in measuring the position of the surface of a sample liquid while it oscillates.

As noted previously with respect to FIG. 3, when the surface of a liquid is excited with a beam of focused acoustic energy, the surface begins to rise. If the surface is excited with enough energy, a drop of liquid can be ejected from the surface of the liquid. However, if less energy is used and a drop of liquid is not forced to be ejected, the surface will simply be raised. If the focused acoustic beam ceases to stimulate the surface, then the surface will continue to rise until the force of the surface tension counters the momentum of the surface. The acoustic energy used to cause the surface to rise, but not eject a drop of liquid is referred to as an excitation burst 321 (the excitation burst 321 is shown in FIG. 8).

Figure 7:
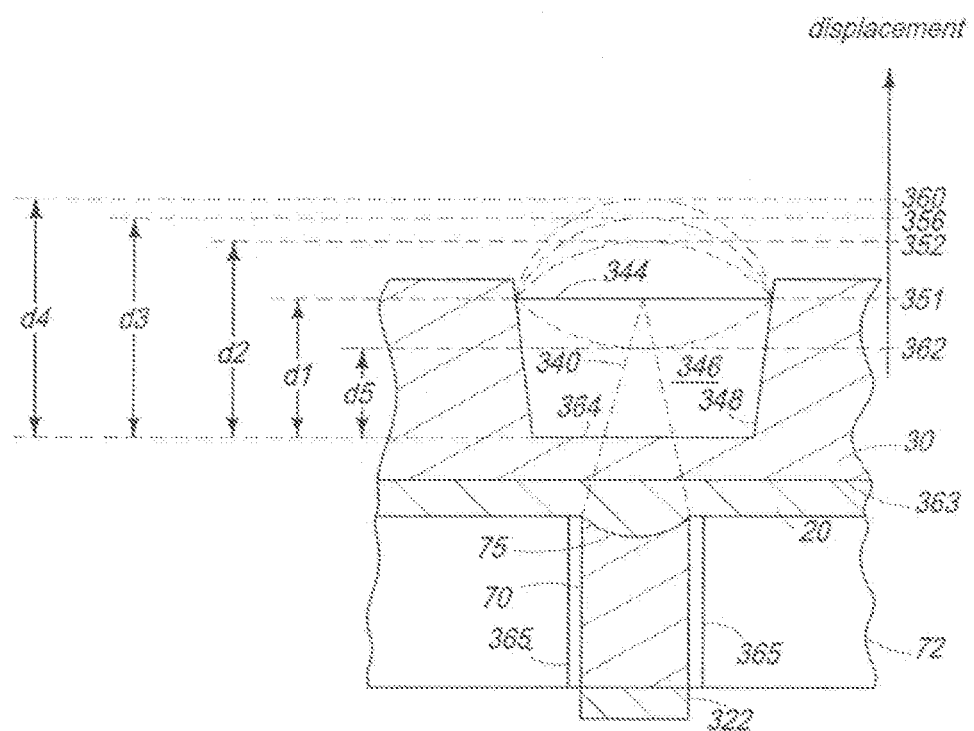
FIG. 7 is a schematic cross-sectional diagram illustrating part of a system for acoustically measuring the position of the surface of a sample liquid while it oscillates.

FIG. 7 schematically illustrates a preferred embodiment for determining the surface tension and viscosity of a liquid. In FIG. 7, elements that are identical to those described previously with respect to FIGS. 1-5 are labeled with the same numerals that were used previously in FIGS. 1-5. In FIG. 7, a focused beam of acoustic energy 340 is focused near a surface 344 of a sample liquid 346 contained in a well 348. Before it is excited, the surface 344 has a first position 351. The focused beam 340 is generated by the excitation burst 321 and causes the surface 344 to begin rising. After exciting the surface 344, the focused beam 340 is discontinued and the surface 344 continues to rise as was explained previously. A second position 352 indicates the height (displacement) of the approximate center of the surface 344 relative to the flat (unexcited) position 351 of the surface 344 as the surface 344 begins to rise in response to the energy being supplied by the focused beam 340. A third position 356 indicates the height of the approximate center of the surface 344 as it rises further after the beam 340 has been turned off, and a fourth position 360 indicates the height of the approximate center of the surface 344 at its maximum height.

The positions 351, 352 and 356 not only illustrate the movement of the surface 344 as it rises initially, but also illustrate positions the surface 344 may move through as it oscillates after the initial rise. Of course the surface 344 moves through many other positions during oscillation, including positions that are lower than position 351, such as a position 362. The sample liquid 346 is analogous to the source fluid 40 described previously with respect to FIG. 2, but is identified differently in FIG. 7 to emphasize that the sample liquid 346 is not necessarily dispensed as a droplet. In addition to the liquids described previously for the source fluid 40, the sample liquid may include many other types of liquids such as paints, epoxies, mixtures, including colloidal suspensions, drinks, such as beers.

Also, in FIG. 7 an interface 363 is shown as the interface between the coupling medium 20 and the containment structure 30. An additional interface 364 is shown as the interface between the containment structure 30 and the sample liquid 346. As a representative example, the containment structure 30 may be a commercially available wellplate, such as the ChemLib™ 1536-well microplate available from Aurora Discovery, Inc. The coupling medium 20 may be a liquid such as water, and in a representative embodiment, has a thickness in the range of three to twelve millimeters. The thickness of the coupling medium 20 varies as necessary as the relative position of the containment structure 30 to the waveguide 70 is altered to achieve the lens 75 to surface 344 distance required for the surface 344 to be stimulated. The waveguide 70 is preferably surrounded by an air-filled gap 365 to reduce reflected acoustic signals from the edges of the waveguide 70.

A plurality of distances $d_1$, $d_2$, $d_3$, $d_4$ and $d_5$ are also illustrated in FIG. 7. The distance $d_1$ represents the distance from the interface 364 to the surface 344 at the position 351. Similarly, the distances $d_2$, $d_3$, $d_4$ and $d_5$ represent the distances from the interface 364 to the surface 344 at the positions 352, 356, 360 and 362, respectively. In general, a distance d is said to represent the distance from the interface 364 to the surface 344 wherever the position of the surface 344 may be in an oscillation cycle, including the position 351 which also indicates the position of the surface 344 at rest before application of the excitation burst 321.

To understand the response of the surface 344 to the energy being supplied by the focused beam 340, it is noted that the surface of a liquid contained in a vessel having a circular cross section at the top of the vessel can be described as a circular membrane. The oscillation modes of a circular membrane have been studied extensively and can be characterized as symmetric and asymmetric oscillation modes. If the circular membrane is excited in the center, then the symmetric modes are excited, and the asymmetric modes remain quiet.

In the embodiment shown in FIG. 7, the well 348 has the shape of a truncated cone and therefore the surface 344 has a circular shape. Thus, the circular membrane model can be applied to the surface 344. The approximate geometric center of the surface 344 is excited with the beam 340 which has sufficient energy to cause the surface 344 to begin to rise, but not enough energy to cause a droplet to be ejected from the surface. Once the surface 344 has been excited, the beam 340 is turned off and the surface 344 continues to rise through the position 356 to position 360.

After the surface 344 has been excited, several modes of vibration begin to oscillate. Following the circular membrane model, the lowest frequency mode is known as the (0, 1) mode and is a symmetric mode. The frequency of this oscillation is dependent on the diameter of the well, and on the surface tension of the liquid in the well. The higher the surface tension, or the smaller the well diameter, the higher the frequency of oscillation. The (0, 2) and (0, 3) modes also contribute to the symmetric oscillation of a circular membrane. The (0, 2) mode oscillates at approximately twice the frequency of the (0, 1) mode, and the (0, 3) mode oscillates at approximately 3.5 times the frequency of the (0, 1) mode. Similarly, after the surface 344 has been excited, each of these modes will decay in a short time. How fast these oscillations decay is partially dependent on the diameter of the well and the viscosity of the fluids on both sides of the circular membrane; namely, the air and the liquid in the well.

The vibrational motion can be tracked by making repeated measurements of the position of the surface 344 in the vertical direction, both above and below the position 351 (e.g. at the positions 352, 356, 360 and 362). The position of the surface is measured using a sonar technique. Specifically, an individual measurement of the position of the surface 344 is made by transmitting a short burst (ping) 368 of acoustic energy from the transducer 322, through the sample liquid 346, and to the surface 344 of the sample liquid. As the burst 368 of acoustic energy traverses the path from the transducer 322 to the surface 344, a plurality of reflected signals are generated wherever a change in acoustic impedance is encountered. For example, a reflected signal 370 is generated when the unfocused pulse of acoustic energy hits the lens 75. Then, when the focused beam 340 passes through the interface 363 between the coupling medium and the containment structure (wellplate) 30, a reflected signal 374 is generated.

Similarly, when the focused beam 340 passes through the interface 364 between the containment structure (wellplate) 30 and the sample liquid 346, a reflected signal 375 is generated. Finally, when the focused beam 340 hits the surface 344, a reflected signal 378 is generated. The reflected signals 370, 374, 375 and 378 are detected by the transducer 322 and the time of arrival of each reflected signal is recorded.

As the surface 344 of the liquid oscillates, and the distance d varies as described previously, the time the burst of acoustic energy takes to travel the distance to the surface 344 and back varies proportionally to the distance.

It should be noted that the short burst (ping) 368 is different than the excitation burst 321 used to cause the surface 344 to begin oscillating. Generally, the short burst 368 transmits much less energy to the surface 344 than does the excitation burst 321 because it is undesirable to have the short burst 368 interfere with the oscillation of the surface 344. In a representative example, the short burst 368 includes approximately five cycles of a sine wave. In contrast, the excitation burst 321 comprises eight hundred cycles. However, the short burst 368 is generated in the same manner as the excitation burst 321. Specifically, the short burst 368 begins as a pulse of acoustic energy emitted from the transducer 322 that moves through the wave channel 70 and is focused by the lens 75 into the focused beam 340. Preferably, the position of the fluid containment structure 30 relative to the waveguide 70 is such that focus is suitable for exciting the surface 344, and the short burst 368 is slightly out of focus with respect to the surface 344 as a result. The focus will vary when the surface 344 moves away from the position 351. This lack of focus does not matter as long as the surface 344 can be reliably detected with the short burst (ping) 368.

FIG. 8 schematically illustrates the relationship between the excitation burst 321, the short burst 368 and the reflected signals 370, 374, 375 and 378 as a function of time. FIG. 8 illustrates that the excitation burst 321 imparts significantly more energy to the surface 344 by showing the amplitude and time duration of the excitation burst 321 as being greater than the amplitude and time duration of the short burst 368. The excitation burst 321 and the other signals are shown as one-sided envelopes in FIG. 8.

The group of reflected signals 370, 374, 375 and 378 enclosed within the bracket 356 correspond to the group of signals that are generated when the position 356 of the surface 344 is measured (see FIG. 7). Similarly, the group of reflected signals 370, 374, 375 and 378 enclosed within the bracket 360 correspond to the group of signals that are generated when the position 360 of the surface 344 is measured (see FIG. 7). In practice, additional groups of reflected signals would be generated when other positions of the surface 344 are measured, such as the position 362.

In FIG. 8, a time $\Delta t^*$ represents the time it takes for the focused beam 340 to traverse the distance (d) from the interface 364 at the bottom of the well 348 to the surface 344 plus the time it takes for the reflected signal 378 to travel from the surface 344 back to the interface 364. Hence, $\Delta t^*$ is a transit time for the short burst 368 to travel from the interface 364 to the surface 344 and back to the interface 364. For the grouping 356, the time $\Delta t^*$ is smaller than the corresponding time $\Delta t^*$ in the grouping 360 because the position 360 is farther from the interface 364 than is the position 356. Similarly, the times $\Delta t^*$ for the positions 351 and 352 would be successively greater than the time $\Delta t^*$ for the position 362, if these positions were measured during oscillation of the surface 344. In the preferred embodiment, the time $\Delta t^*$ is measured by electronically processing the reflected signals 375 and 378.

In the preferred embodiment, the distance d does not need to be calculated, so the velocity of sound does not need to be known. However, if desired, the distance (d) can be calculated, if the velocity of sound is known, by using the formula $d = v\Delta t^*/2$, where v is the velocity of sound in the sample liquid and $\Delta t^*$ has the definitions given above. Instead, in the preferred embodiment, the time $\Delta t^*$ is used directly, as it is the underlying measurement of the position of the surface 344 as a function of time relative to the bottom of the well 348 (i.e. the interface 364). In this usage, the time $\Delta t^*$ is referred to as the position in time of the surface 344 relative to the position in time of the bottom of the well 348 (i.e. the interface 364).

Figure 9:
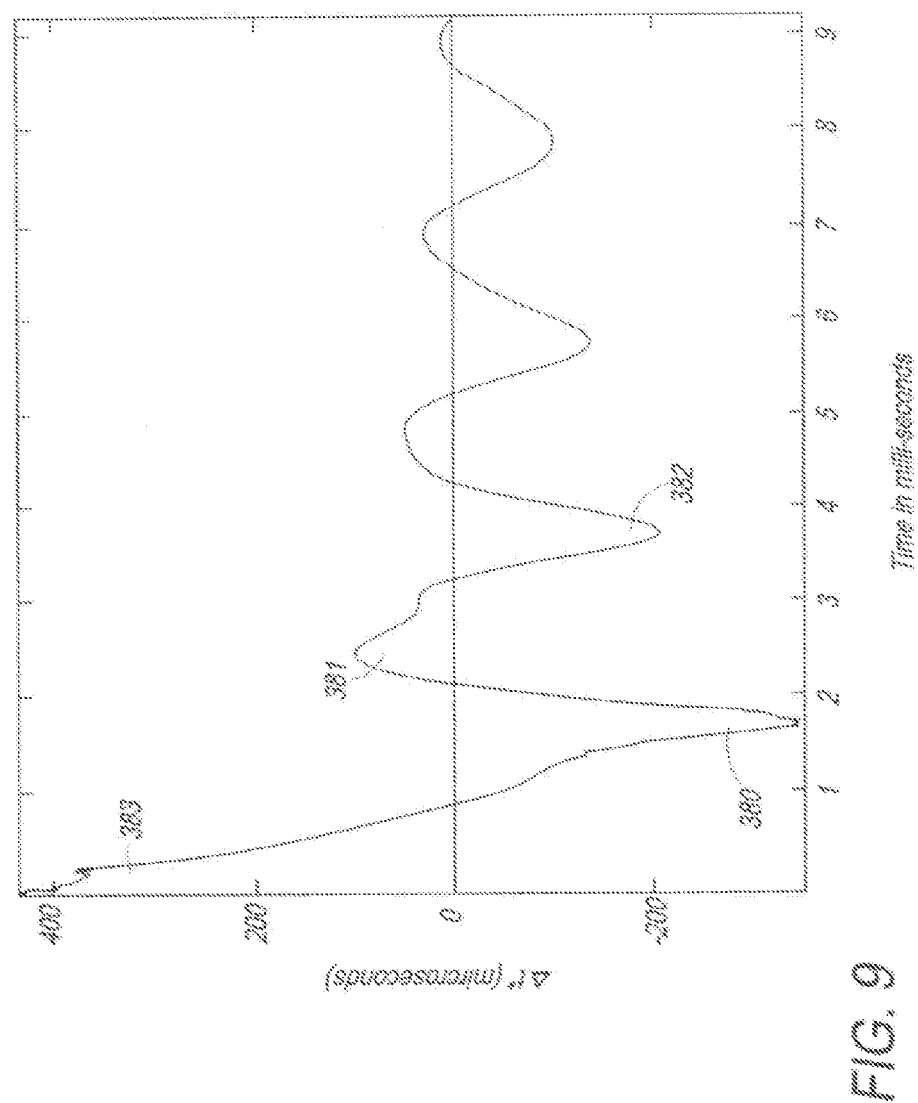
FIG. 9 is a representative graph of position in time versus time.

If the short burst 368 is generated, followed by a pause, and then the reflected signals (such as the reflected signals 370, 374, 375 and 378) are detected, the position in time $\Delta t^*$ can be measured. If this sequence is repeated, the position in time $\Delta t^*$ can be measured over and over as the surface 344 is moving. The result is a time domain data set (i.e. a positional data set) of the position in time of the surface 344 after each measurement, which represents a time domain response of the surface 344. A representative plot of the time domain response (position in time $\Delta t^*$ of the surface 344 versus time) is shown in FIG. 9. The position in time $\Delta t^*$ is the position during the oscillation relative to the time when the surface 344 is at the unexcited position 351. When the position in time $\Delta t^*$ is negative in FIG. 9, the surface 344 is below the unexcited position 351. When the position in time $\Delta t^*$ is positive, the surface 344 is above the unexcited position 351. In an alternative embodiment, the actual position d could be calculated for each measurement (if the speed of sound in the medium is known or determined), and a plot of position d versus time could be made. The resulting plot would have the same shape as the plot shown in FIG. 9. In FIG. 9, several of the peaks have been labeled for reference purposes. Specifically, a peak 380 has a minimum at around 1.7 milliseconds, a peak 381 has a maximum at around 2.4 milliseconds and a peak 382 has a minimum at around 3.8 milliseconds. A peak 383 is the first positive peak in FIG. 9, and has a maximum at around 0 milliseconds.

Once the positional data set of position in time ($\Delta t^*$) versus time has been generated, the dominant modes of the oscillation can be determined from the frequency content of the time domain response. In the preferred embodiment, the frequency content of the oscillation can be extracted from the frequency domain data set. The frequency domain data set comprises an amplitude spectrum and a phase spectrum for the oscillating surface 344. It should be noted that in determining surface tension, only the amplitude spectrum is needed. But viscosity determination requires that both the amplitude spectrum and the phase spectrum be used.

A Fast Fourier Transform (FFT) technique is a well-understood method of obtaining such information (i.e. the amplitude spectrum and the phase spectrum), and is used in the preferred embodiment. Other frequency analysis techniques, including wavelet analysis and other Fourier Transform techniques besides the FFT technique, may also be used to generate the frequency domain data set, as could techniques that utilize an analog hardware system.

Figure 10:
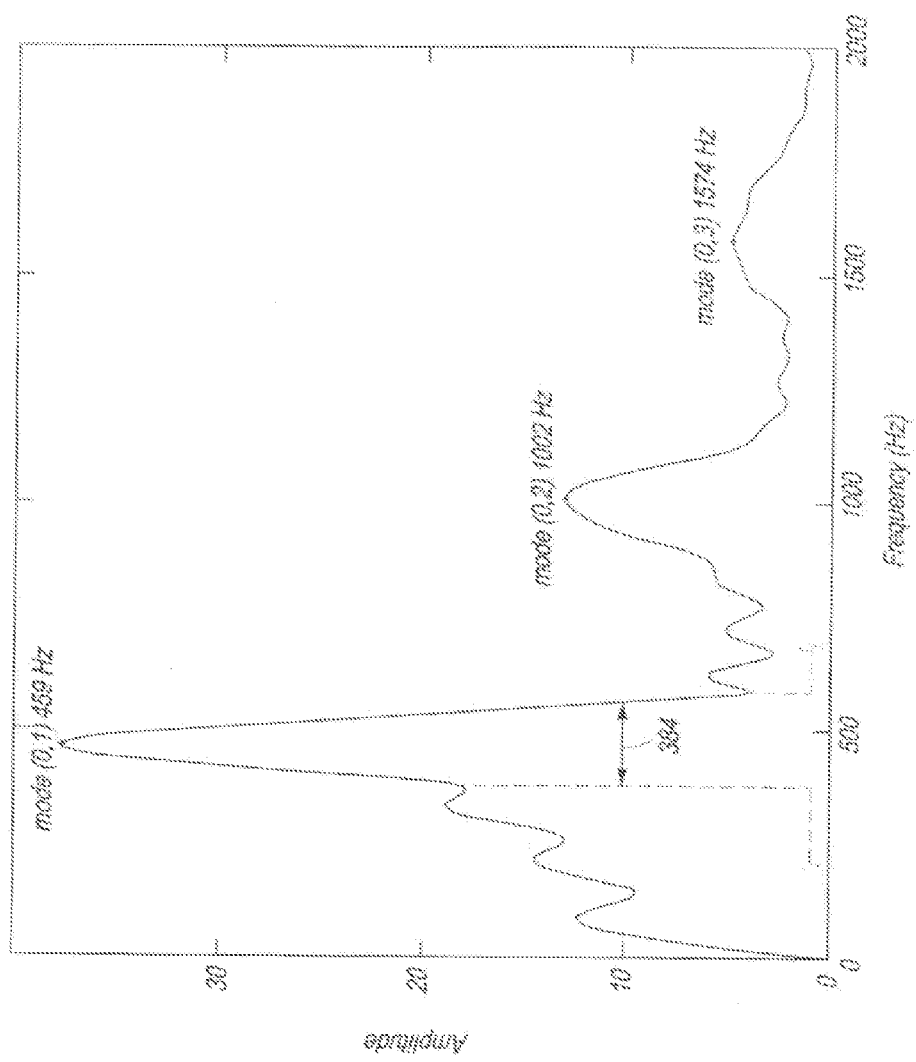
FIG. 10 is a representative graph of the frequency content of the data from FIG. 9.

FIG. 10 is a representative illustration of the amplitude spectrum of the data in FIG. 9 and shows amplitude versus frequency. FIG. 9 shows the relative motion of the surface 344 with respect to the nominal surface position of the surface 344 in FIG. 7. Using the amplitude spectrum data from the FFT, the frequency and the amplitude of the various vibrational modes can be identified and isolated. In FIG. 10, mode (0, 1) is the largest (i.e. has the largest amplitude), and is readily identified as a result. Any other modes of interest can be identified and isolated once mode (0, 1) has been identified using the model of a vibrating circular membrane (i.e. by looking for the maximum amplitudes at the frequency multiples indicated by the model). The frequency corresponding to the maximum amplitude for a mode is referred to as the oscillation frequency. The first three symmetric modes have been identified on FIG. 10 and have oscillation frequencies of 459 Hz, 1002 Hz and 1574 Hz.

It should be noted that in an alternative embodiment, the oscillation frequency of any vibrational mode can also be derived by measuring the time to any of the peaks from the time domain response of the vibrational mode. Furthermore, the oscillation frequency of the fundamental mode (0, 1) can be estimated by such measurement from the positional data set. For example, in FIG. 9, the peak 381 has a maximum at about 2.4 milliseconds which is also approximately the time interval between the first two positive peaks (e.g. peaks 383 and 381). The reciprocal of this time interval ($1/0.0024$ seconds) gives a frequency of 417 Hz, which can be used as the oscillation frequency of the (0, 1) mode. This method is usually less precise than a FFT technique for determining an oscillation frequency, but it is useful in certain situations.

The time domain response of any mode can be determined once the mode has been identified. This is achieved by extracting a narrow range of data from the frequency domain data set centered on the mode of interest; for example, the frequency range 384 shown in FIG. 10 for mode (0, 1). This narrow range of data can be extracted, for example, by applying a filter to the data of FIG. 10 so that data outside the frequency range 384 is not used. An Inverse Fast Fourier Transform (IFFT) is performed on this narrow range of data to isolate the time domain response of the mode of interest. For example, if the IFFT is performed on the frequency range 384, the time domain response of the (0, 1) mode is isolated. It should be noted that in alternative embodiments, rather than performing FFT/IFFT processing, the time domain response of a vibrational mode can also be obtained by filtering the positional data set in the time domain. For example, in FIG. 9 a low pass filter, which allows the mode (0, 1) oscillation frequency to pass, could be used to get the time domain response of the fundamental mode (0, 1).

Figure 11:
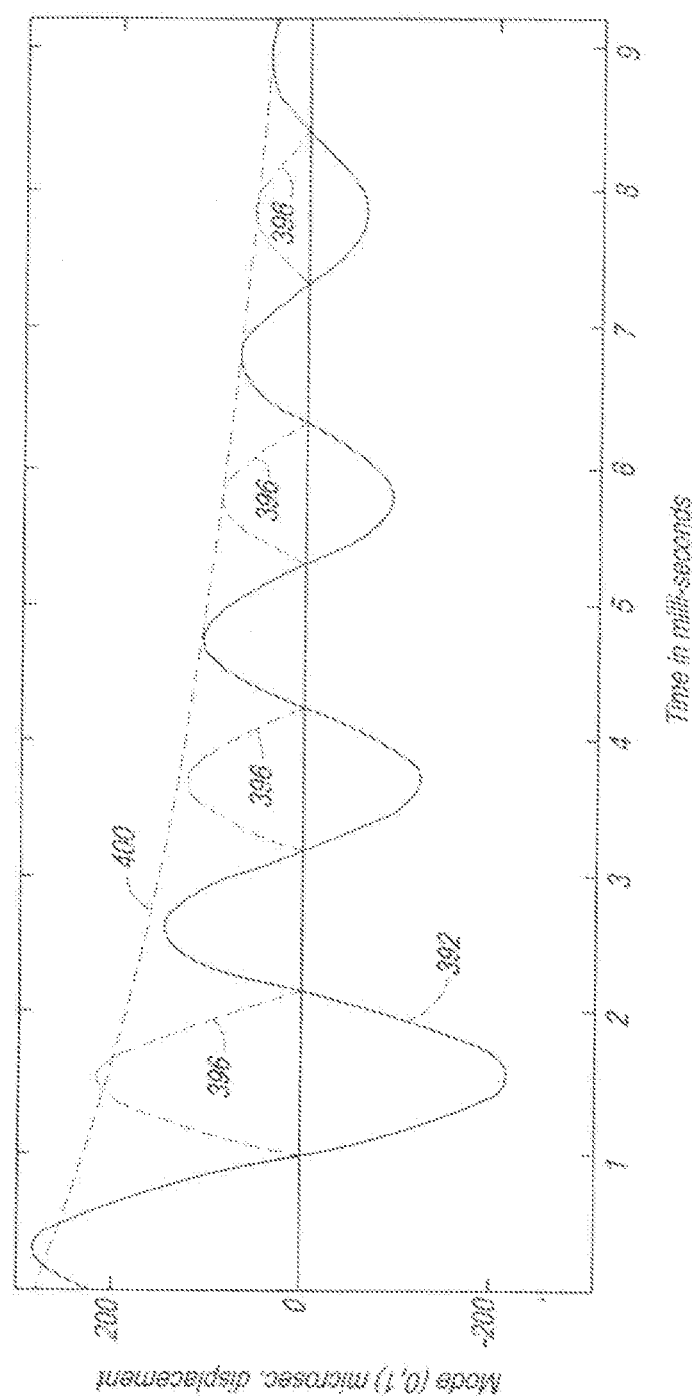
FIG. 11 is a representative graph illustrating the motion of a single frequency mode from the data of FIG. 10 versus time.

The output of the IFFT is a time domain data set comprised of displacement amplitude (in microseconds) versus time, and shown as the waveform 392 in FIG. 11. The waveform 392, shown in FIG. 11, illustrates the motion of the mode (0, 1) component of the oscillation versus time. The decay time constant of the mode is determined as shown in FIG. 11 by inverting the polarity of the negative peaks of the waveform 392 (illustrated as waveform 396) and performing an exponential curve fit to the positive peaks of waveforms 392 and 396 (illustrated as curve 400).

Information such as that shown in FIGS. 10 and 11 is used to determine the proportional changes in surface tension (T) and the viscosity ($\eta$) of the liquid. To determine these parameters, the displacement motion of a symmetrical mode is modeled using a mass-spring-damper model.

The mass-spring-damper model yields the following proportionality equations for the surface tension (T) and the viscosity ($\eta$) of the liquid, equations 1 and 2, respectively.

$$T \propto d\omega^2 r^2 \quad (1)$$

$$\eta \propto dr^2/\tau \quad (2)$$

Where r is the radius of a well at the surface 344; d is the surface density of the liquid; $\omega$ is the natural angular frequency of the vibrational mode ($\omega=2\pi f$, f is the natural frequency of the vibrational mode); and $\tau$ is the decay time constant. The damped natural angular frequency ($\omega^*$, where $\omega^*=2\pi f^*$) is obtained from the Fast Fourier Transform (FFT) data. The damped natural frequency (f*) is the measured oscillation frequency for the vibrational mode, such as the 459 Hz frequency for the (0, 1) mode shown in FIG. 10. When the damping factor ($\xi$) is small, the natural angular frequency $\omega$ is approximately equal to the damped natural angular frequency $\omega^*$.

In a preferred embodiment of the present invention, the steps involved in a frequency domain method for determining the surface tension and/or viscosity of a liquid contained in a cylindrically shaped container include:

a) exciting a surface of a liquid (for example, surface 344) contained in a container (for example, the well 348);

b) generating a positional data set (for example, $\Delta t^*$ versus time as shown in FIG. 9) comprised of a plurality of positional measurements related to the position of the surface at a plurality of times after the surface is excited;

c) generating a frequency domain data set from the positional data set with the frequency domain data set comprising information about the oscillation frequency of at least one vibrational mode of the surface as it oscillates. For example, the frequency domain data set may comprise an amplitude spectrum for one or more vibrational modes as illustrated in FIG. 10; and d) processing the frequency domain data set to yield information about the surface tension and/or viscosity of the liquid (for example, equations 1 and 2).

In step "d," the processing step could include the identification of the oscillation frequency for a vibrational mode; using the oscillation frequency to calculate the surface tension, such as with equation 1; applying the IFFT to the narrow range of frequency domain data to get the time domain response of the vibrational mode; processing the time domain response to get the decay time constant; and using the decay time constant to determine the viscosity, such as with equation 2.

In another embodiment of the present invention, the positional data set is processed directly to yield surface tension and/or viscosity information without generating a frequency domain data set. The steps involved in a time domain method for determining the surface tension and/or viscosity of a liquid contained in a cylindrically shaped container include:

a) exciting a surface of a liquid (for example, surface 344) contained in a container (for example, the well 348);

b) generating a positional data set (for example, $\Delta t^*$ versus time as shown in FIG. 9) comprised of a plurality of positional measurements related to the detected position of the surface at a plurality of times after the surface is excited; and c) processing the positional data set to yield information about the surface tension and/or viscosity of the liquid.

In step "c," the processing step could include the identification of the oscillation frequency for a vibrational mode, for example by measuring the time to a peak in the positional data set, or by measuring the time interval between peaks. For example, in FIG. 9, the peak 381 has a maximum at about 2.4 milliseconds. The reciprocal of this time interval ($1/0.0024$ seconds) gives a frequency of 417 Hz, which can be used as the oscillation frequency of the (0, 1) mode. The processing step could also include using the oscillation frequency to calculate the surface tension, for example with equation 1; filtering the positional data set to get the time domain response of the fundamental mode (0, 1); processing the time domain response to get the decay time constant; and using the decay time constant to determine the viscosity, for example with equation 2.

It should also be noted that various mixed mode methods of determining surface tension and viscosity may be used. For example, the surface tension can be measured using the frequency domain method, and the viscosity can be measured using the time domain method with a filter set by the oscillation frequency of the fundamental mode (0, 1). In another embodiment, the surface tension is measured using the time domain method, and the viscosity is measured using the frequency domain method.

Although the present invention has been described in terms of the presently preferred embodiments, it is to be understood that such disclosure is not to be interpreted as limiting. Various parts of the present invention can be implemented in hardware, software, microcode, digital signal processing (DSP), or combinations of these techniques. Various alterations and modifications will no doubt become apparent to those skilled in the art after having read the above disclosure. Accordingly, it is intended that the appended claims be interpreted as covering all alterations and modifications as fall within the true spirit and scope of the invention.

We claim:

1. A method for determining the surface tension and/or viscosity of a liquid comprising the steps of:

a) exciting a surface of a liquid contained in a container with an excitation burst of acoustic energy that causes the surface to oscillate;
b) discontinuing the excitation burst after the surface begins to oscillate;
c) reflecting a plurality of short bursts of acoustic energy off of the surface over a period of time while the surface is oscillating;
d) generating a positional data set comprised of a plurality of positional measurements related to the position of the surface at a plurality of times after the surface is excited, the positional data set being derived from information generated by the plurality of short bursts; and
e) processing the positional data set to yield information about the surface tension and/or viscosity of the liquid.

2. The method of claim 1 wherein the positional data set includes one or more peaks in a time domain response, and wherein the processing of the positional data set in step "e" comprises determining the oscillation frequency of a first vibrational mode by measuring the time to one of the peaks or a time interval between two or more peaks in the positional data set.

3. The method of claim 2 further comprising the step of: processing the oscillation frequency to yield information about the surface tension of the liquid.

4. The method of claim 3 wherein the surface tension is obtained using a relationship of the form $T \propto d\omega^2 r^2$, where T is the surface tension, r is the radius of a well at the surface of the liquid, d is the surface density of the liquid, and $\omega$ is thenatural angular frequency of the vibrational mode and is related to the oscillation frequency.

5. The method of claim 2 further comprising the steps of:
extracting a time domain response of the first vibrational mode from the positional data set by filtering;
extracting a decay time constant from the time domain response of the first vibrational mode; and
processing the decay time constant of the time domain response of the first vibrational mode to yield information about the viscosity of the liquid.

6. The method of claim 5 wherein the viscosity is obtained using a relationship of the form $\eta \propto dr^2/\tau$, where $\eta$ is the viscosity, r is the radius of a well at the surface of the liquid, d is the surface density of the liquid, and $\tau$ is the decay time constant.

7. A method for determining the surface tension and/or viscosity of a liquid comprising the steps of:
a) exciting a surface of a liquid contained in a container with an excitation burst of acoustic energy that causes the surface to oscillate;
b) generating a positional data set comprised of a plurality of positional measurements related to the position of the surface at a plurality of times after the surface is excited;
c) generating a frequency domain data set from the positional data set; and
d) processing the frequency domain data set to yield information about the surface tension and/or the viscosity of the liquid.

8. The method of claim 7 wherein the excitation burst is focused into an acoustic beam that is propagated through the liquid and towards the surface.

9. The method of claim 7 wherein each positional measurement is made by directing a short burst of acoustic energy at the surface as it oscillates and determining the time required for the short burst to travel through the liquid to the surface.

10. The method of claim 7 wherein a Fast Fourier Transform technique is used in step "c" to generate the frequency domain data set from the positional data set.

11. The method of claim 7 wherein the processing of the frequency domain data set in step "d" comprises determining an oscillation frequency of a first vibrational mode of the surface when it oscillates.

12. The method of claim 11 wherein the oscillation frequency of the first vibrational mode is used to determine the surface tension of the liquid.

13. The method of claim 11 wherein the processing of the frequency domain data set in step "d" further comprises the steps of:
extracting a narrow range of the frequency domain data set centered on the first vibrational mode;
applying an Inverse Fast Fourier Transform technique to the narrow range of the frequency domain data set to get a time domain response of the first vibrational mode;
determining the decay time constant of the first vibrational mode; and
using the decay time constant to determine the viscosity of the liquid.

14. The method of claim 11 wherein the first vibrational mode comprises the lowest frequency symmetric mode.

15. The method of claim 12 wherein the surface tension is determined using a relationship of the form $T \propto d\omega^2 r^2$, where T is the surface tension, r is the radius of a well at the surface of the liquid, d is the surface density of the liquid, and $\omega$ is the natural angular frequency of the vibrational mode and isrelated to the oscillation frequency.

16. The method of claim 13 wherein the viscosity is determined using a relationship of the form $\eta \propto dr^2/\tau$, where $\eta$ is the viscosity, r is the radius of a well at the surface of the liquid, d is the surface density of the liquid, and $\tau$ is the decay time constant.

17. A method for determining the surface tension and/or viscosity of a liquid comprising the steps of:
a) exciting a surface of a liquid contained in a container with an excitation burst of acoustic energy that causes the surface to oscillate;
b) generating a positional data set comprised of a plurality of position in time measurements for the surface at a plurality of times after the surface is excited, the position in time measurements being made by directing short bursts of acoustic energy at the surface and determining the transit time required for the short burst to travel through the liquid to the surface and back through the liquid;
c) using a Fast Fourier Transform technique to generate a frequency domain data set from the positional data set, the frequency domain data set comprising an amplitude spectrum for the surface as it oscillates;
d) using the amplitude spectrum to determine an oscillation frequency of a first vibrational mode; and
e) using the oscillation frequency of the first vibrational mode to determine the surface tension of the liquid.

18. The method of claim 17 further comprising the steps of:
f) selecting a narrow range from the frequency domain data set centered on the first vibrational mode;
g) applying an Inverse Fast Fourier Transform technique to the narrow range to yield a time domain response of the first vibrational mode;

h) determining the decay time constant from the time domain response of the first vibrational mode; and i) using the decay time constant of the time domain response to determine the viscosity of the liquid.

19. The method of claim 17 wherein the surface tension in step "e" is determined using a relationship of the form $T \propto d\omega^2 r^2$, where T is the surface tension, r is the radius of a well at the surface of the liquid, d is the surface density of the liquid, and $\omega 0$ is the natural angular frequency of the vibrational mode.

20. The method of claim 18 wherein the viscosity in step "i" is determined using a relationship of the form $\eta \propto dr^2/\tau$, where $\eta$ is the viscosity, r is the radius of a well at the surface of the liquid, d is the surface density of the liquid, and $\tau$ is the decay time constant.

21. The method of claim 17 wherein the first vibrational mode comprises the lowest frequency symmetric mode.

* * * * *